(12) United States Patent
Kim

(10) Patent No.: US 9,724,209 B2
(45) Date of Patent: Aug. 8, 2017

(54) SPHERICAL-ARC ROTATING SAW BLADE POWER TOOL FOR ACETABULAR CUP EXTRACTION

(71) Applicant: Infinesse Corporation, Los Angeles, CA (US)

(72) Inventor: Chong Chol Kim, Los Angeles, CA (US)

(73) Assignee: Infinesse, Corporation, Los Angeles, CA (US)

( * ) Notice: Subject to any disclaimer, the term of this patent is extended or adjusted under 35 U.S.C. 154(b) by 176 days.

(21) Appl. No.: 14/154,330

(22) Filed: Jan. 14, 2014

(65) Prior Publication Data

US 2015/0196402 A1 Jul. 16, 2015

Related U.S. Application Data

(60) Provisional application No. 61/751,656, filed on Jan. 11, 2013.

(51) Int. Cl.
*A61F 2/46* (2006.01)
*A61B 17/16* (2006.01)

(52) U.S. Cl.
CPC ........ *A61F 2/4609* (2013.01); *A61B 17/1666* (2013.01); *A61F 2002/4619* (2013.01)

(58) Field of Classification Search
CPC ............... A61B 17/1666; A61F 2/4609; A61F 2002/4619
See application file for complete search history.

(56) References Cited

U.S. PATENT DOCUMENTS

| | | | | |
|---|---|---|---|---|
| 3,147,749 A | * | 9/1964 | Marsh | A61B 10/0291 30/187 |
| 5,830,215 A | * | 11/1998 | Incavo | A61B 17/1637 606/79 |
| 2006/0200165 A1 | | 9/2006 | Tulkis | |
| 2008/0195111 A1 | | 8/2008 | Anderson | |
| 2012/0184964 A1 | | 7/2012 | Hudak, Jr. et al. | |
| 2015/0359641 A1 | * | 12/2015 | Nic | A61F 2/4609 606/81 |

OTHER PUBLICATIONS

World Intellectual Property Organization, International Search Report and Written Opinion for International Application No. PCT/US2014/011325, mail date Apr. 17, 2014, pp. 1-9.

* cited by examiner

*Primary Examiner* — David Bates
*Assistant Examiner* — Olivia C Chang
(74) *Attorney, Agent, or Firm* — SoCal IP Law Group LLP; Michael D. Harris

(57) ABSTRACT

To remove a damaged acetabular cup attached to the hipbone, applicant positions the cutting surface of a curved cutting blade at the acetabular cup/hipbone interface. The blade mounts to a head. The powered drive shaft of a motor rotates the blade and head. A linkage, part of which may be around the drive shaft, moves longitudinally relative to the drive shaft under surgeon control. The linkage pivots the head and urges the blade into the interface. As the power tool rotates the curved blade and the linkage pivots the blade into the interface, the blade follows the hemispherical contour of the interface. Continued powered rotation of the drive shaft and blade and further pivoting of the blade cuts the cup from the hipbone.

38 Claims, 11 Drawing Sheets

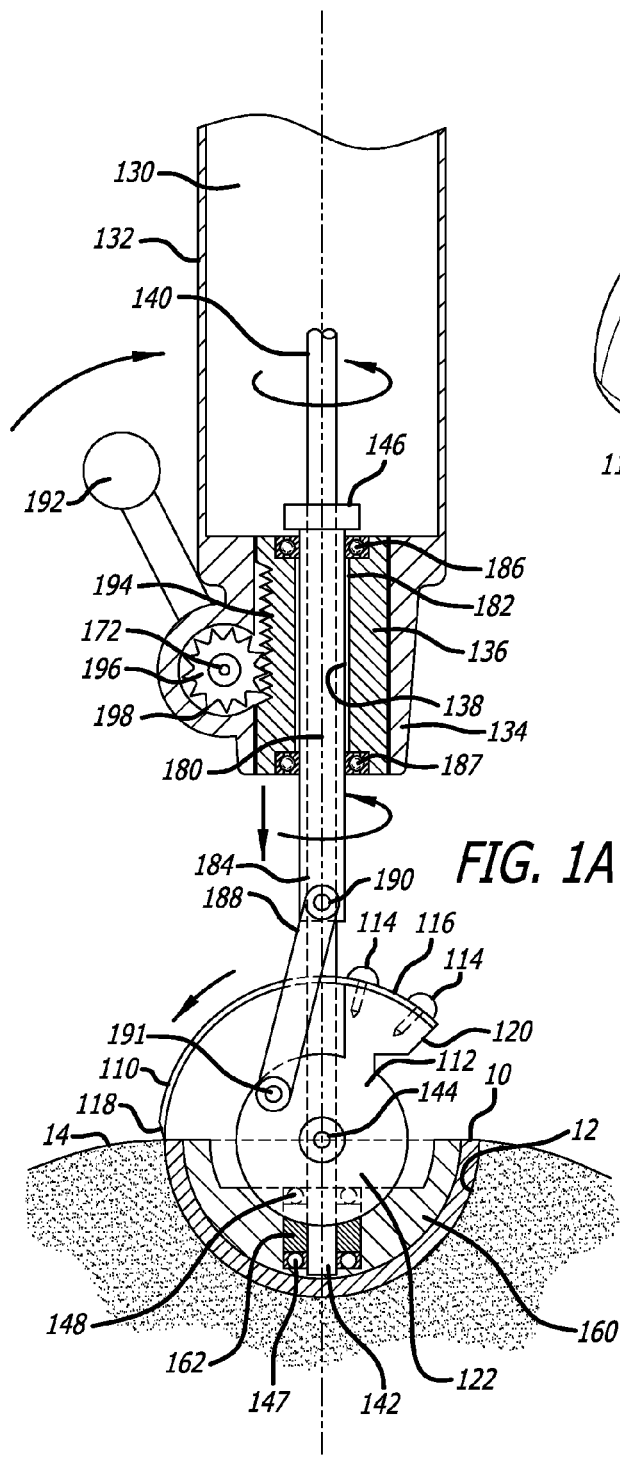
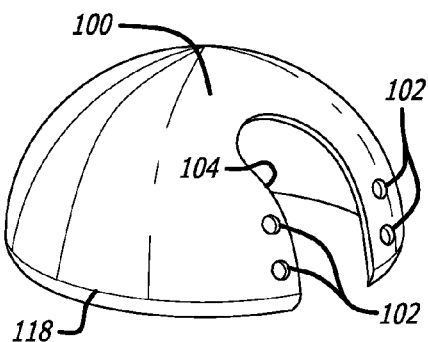
FIG. 1A
FIG. 1B
© 2014 Infinesse Corp.
© 2014 Infinesse Corp.

© 2014 Infinesse Corp.

SPHERICAL-ARC ROTATING SAW BLADE POWER TOOL FOR ACETABULAR CUP EXTRACTION

BACKGROUND

1. Field

Orthopedic tools especially for removing damaged prosthetic acetabular cups.

2. Related Application

Applicant claims the benefit of provisional application No. 61/751,656, filed 11 Jan. 2013 and International application No. PCT/US2014/011325.

3. General Background and State of the Art

Total hip replacement surgery in which the hip joint is replaced by a prosthetic implant is a common orthopedic procedure. It is usually performed to relieve arthritis pain or because of hip fracture. Total hip replacements use two components, a femoral stem and an acetabular socket or cup. To insert the femoral stem, a surgeon removes the proximal end of the femur and shapes the end to receive the stem. The stem also has a ball or femoral head attached. Titanium, cobalt chromium and stainless steel are the most common stem materials. Metal or ceramic materials are common for the head.

The surgeon also removes cartilage and bone from the hip socket and then secures a prosthetic acetabular cup or socket into the hip socket using friction, cement or ingrowth material. Some acetabular cups are one piece; others are modular. They usually are high-density polyethylene or metal.

Most total hip replacements work very well. However, problems can arise especially many years after the surgery when the patient outlives the replacement. Those problems are more common when young adults have hip replacements following athletic injuries or accidents. However, persons who have hip replacements when they are older also can outlive their hip replacements. Then the patient may need a second hip replacement. A third hip replacement may be required in some circumstances.

When a surgeon preforms a second or third hip replacement, he or she must remove the existing acetabular cup. All methods for removing it are manual. One device for removing the acetabular cup is the Explant® acetabular cup removal system, sold by Zimmer, Inc. See http://www.zimmer.com/content/pdf/en-US/Explant_Acetabular_Cup_Removal_System_Surgical_Technique_%2897-7255-206-00%29%2810_2011%29.pdf (accessed Aug. 21, 2012). It includes a shank with an alignment head at the distal end. The head fits into the existing acetabular cup. A strong, rigid, curved blade, which is sized to conform to the acetabular cup, mounts to a fitting on the shank. The blade is spaced from the shank to fit between the outside of the acetabular cup and the hipbone. The surgeon works the blade between the acetabular cup and the hipbone until the blade is inserted to its maximum. The device also has a handle perpendicular to the shank. After the blade is fully inserted into the acetabular cup, the surgeon applies force to the handle to rotate the blade causing the blade to move along the bone/acetabular cup interface until it travels fully about the acetabular cup. That releases the acetabular cup for removal by the surgeon.

This technique is time consuming. An hour is common just for this preliminary work. Minimizing time in surgery especially under anesthesia is usually desirable. In addition, the hipbone behind the acetabular cup is thin. Especially for patients with osteoporosis, the force used with this technique can damage the hipbone.

SUMMARY

The device removes a damaged acetabular cup that had been attached to the hipbone earlier during total hip replacement surgery. The device is powered and uses a generally hemispherical blade. The blade mounts to a head, and a drive shaft connected to a motor rotates the blade and head. The blade's cutting surface is positioned at the acetabular cup/hipbone interface. A linkage associated with the drive shaft can move longitudinally relative to the drive shaft. That movement pivots the head, which carries the blade into the interface. Continued rotation of the drive shaft and blade cuts through the cup/bone interface to free the cup.

The linkage may include a sleeve around the drive shaft, and a mechanism can move the sleeve relative to the drive shaft. Arms may connect the sleeve to the head. The arms are angled relative to the axis of the sleeve and drive shaft. Therefore, as the sleeve drives the arms, the arms pivot the head and blade.

BRIEF DESCRIPTION OF THE DRAWINGS

FIG. 1A is a side, partially sectioned view of applicant's tool for acetabular cup extraction.

FIG. 1B is a plan view of a blade for the tool for acetabular cup extraction.

Insofar as different drawings show similar components, the components may not be numbered in all figures.

DETAILED DESCRIPTION

A previously installed and damaged metal or plastic acetabular cup 10 seats in socket 12 in hip 14 (FIG. 1A).

Cups usually come in different sizes, and the surgeon chooses the size for each patient. When the acetabular cup was installed originally, it was secured to the hipbone with cement or porous ingrowth material. To remove the acetabular cup, a tool must break the cup/bone interface.

Applicant's tool may be considered to include three major components, (1) a blade, (2) a motor and drive shaft for rotating the blade and (3) a linkage for pivoting the rotating blade through the acetabular cup/bone interface.

Figure 10:
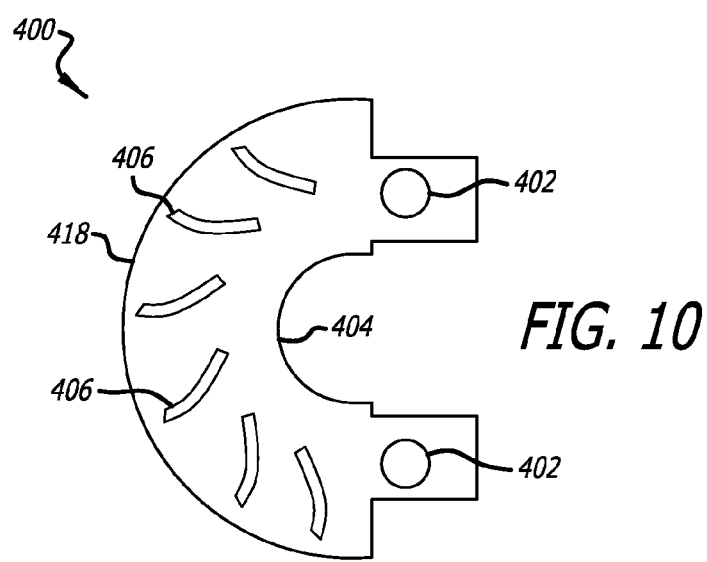
FIG. 10 is a plan view of a blade used in applicant's acetabular cup extraction tool.

The blade component includes blade 100 itself (FIG. 1B). See also blade 400 in FIG. 10. The blades are hemispherical in the drawings to conform to the hemispherical acetabular cup/bone interface. Different size blades should be available to accommodate difference different sized cups. If the acetabular cup/bone interface is not hemispherical, the curvature edge the blade may change to accommodate the curvature of the acetabular cup/bone interface. In addition, though the blades shown in FIGS. 1B and 10 extend almost fully around to be hemispherical, the blade could be narrower and may conform to a segment of a sphere. A narrower blade still will traverse acetabular cup/bone interface as it rotates.

Figure 11:
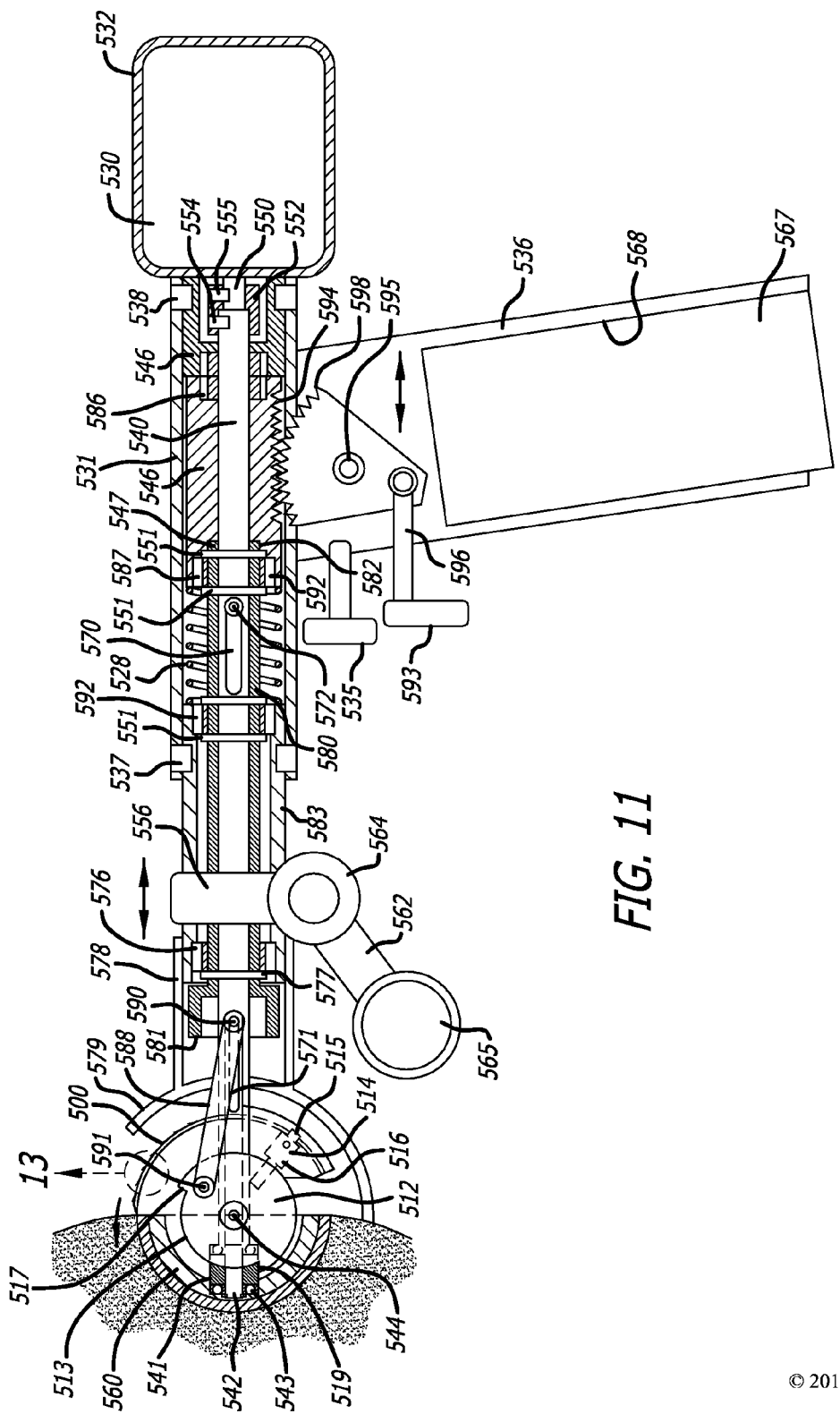
FIG. 11 is a side, partially sectioned view of another version of applicant's acetabular cup extraction tool.

The distal end of blade 100 includes a sharp, possibly serrated, cutting edge 118 (FIG. 1A). See also edge 418 in FIG. 10. The blade may be disposable. FIG. 11 shows special teeth on blade 500, which are explained in more detail in the discussion of that figure. Those special teeth can be used for the blades in the other figures.

A motor causes spindle or drive shaft 140 to rotate, and blade 100 (FIGS. 1A and 1B) rotates with the drive shaft about the shaft's longitudinal axis. The blade also is mounted for pivoting about the axis perpendicular to the drive shaft's longitudinal axis (i.e. horizontal axis in FIG. 1A) between the FIG. 1A and FIG. 2 positions.

Figure 12:
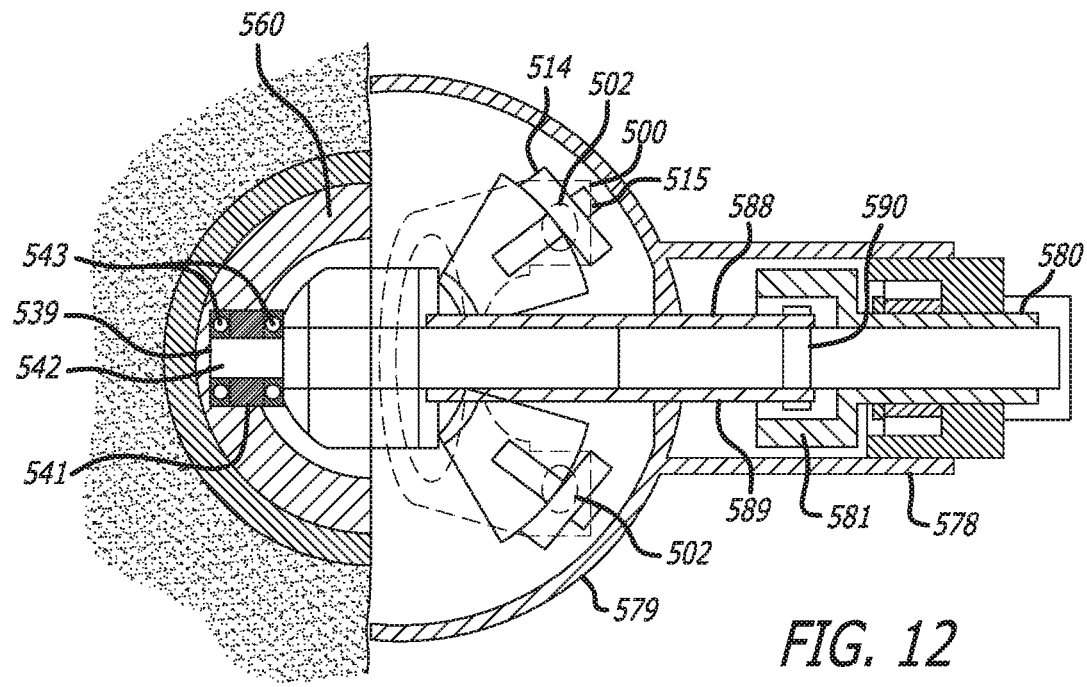
FIG. 12 is a front, partially sectioned view of the distal end of applicant's acetabular cup extraction tool shown in FIG. 11.

Blade 100 is fastened or otherwise is attached to upper portion 120 of head 112 (FIG. 1A). The head is a hub assembly fixture that integrates several components as explained in more detail. Quick-release or other fasteners 114 extend through openings 102 (FIG. 1B) in proximal end 116 of the blade to secure the blade to the head. The tools in FIGS. 8 and 12, which are discussed in conjunction with descriptions of those figures, show more detail of quick-release fasteners.

The motor component includes electric motor 130 or other motive device, which rotates spindle or drive shaft 140 about the longitudinal axis of the drive shaft. The axis sometimes is referred to as the "first axis." The motor may be a low-speed, high torque motor. Motor 130 may connect to an A/C outlet, a swappable battery pack or other portable power source. Pneumatic or hydraulic motors also can be used. In FIG. 1A, the motor is within metal or plastic housing 132. The housing material should be resistant to corrosion and be able to be sterilized. The outer surface of the housing may have curves, roughened or knurled surfaces or structures to make holding the housing easier. The pistol-shaped housing in FIGS. 6, 7, 8 and 11 are examples of housings that are easier to grip.

Drive shaft 140 may be fixed to or removable from the motor. If it is removable, the attachment of the drive shaft to the motor can be designed for quick attachment and release. The tool shown in FIGS. 1A and 2 could use structure shown in other drawings for operably connecting the motor to the drive shaft.

As motor 130 rotates drive shaft 140, blade 100 (FIGS. 1A and 1B) rotates with the drive shaft about the shaft's longitudinal axis. The blade also is mounted for pivoting about the axis perpendicular to the drive shaft's longitudinal axis (i.e. horizontal axis in FIG. 1A) between the FIG. 1A and FIG. 2 positions.

Figure 2:
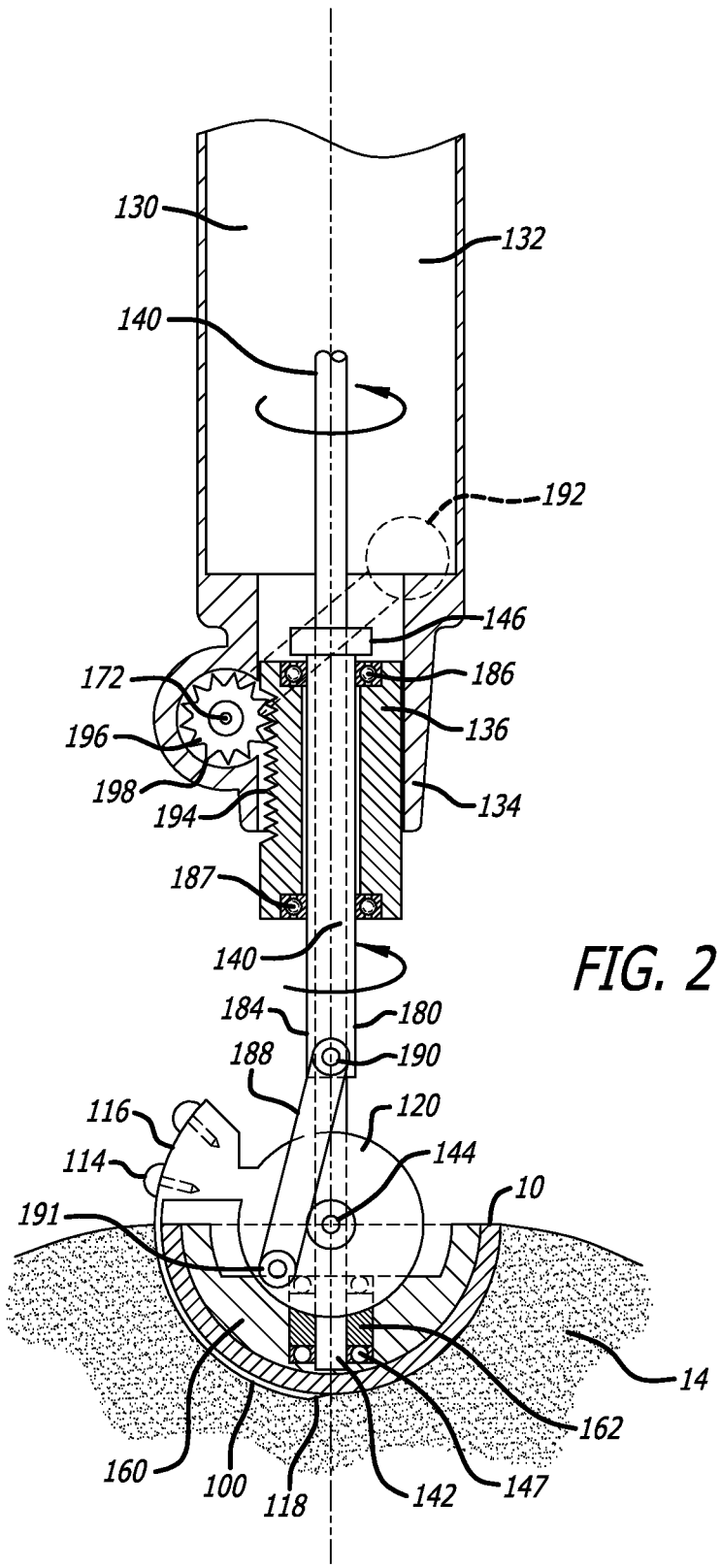
FIG. 2 also is a side, partially sectioned view of applicant's acetabular cup extraction tool shown in FIG. 1. The blade in this figure has pivoted to another position than the blade shown in FIG. 1A.
Figure 3:
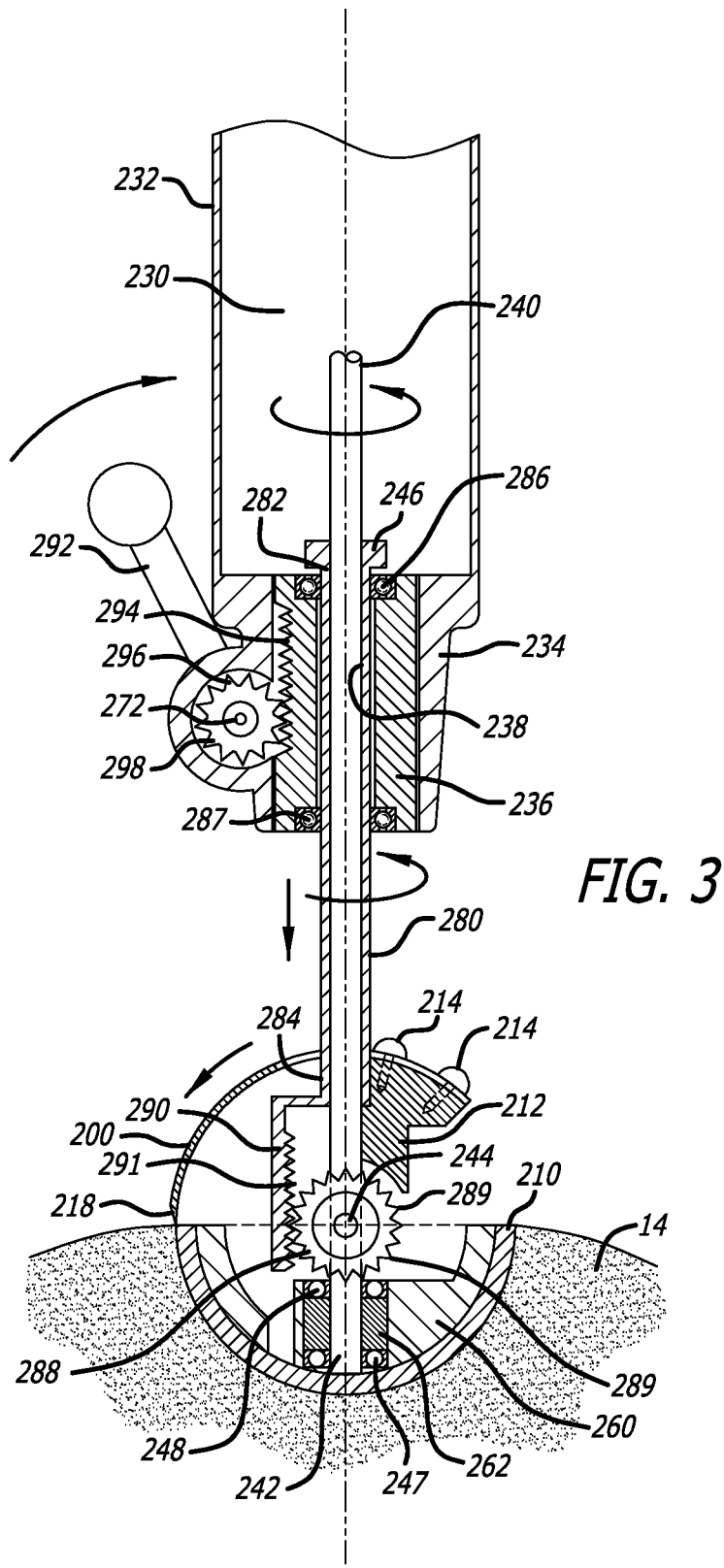
FIG. 3 also is a side, partially sectioned view of a different version of applicant's acetabular cup extraction tool.
Figure 4:
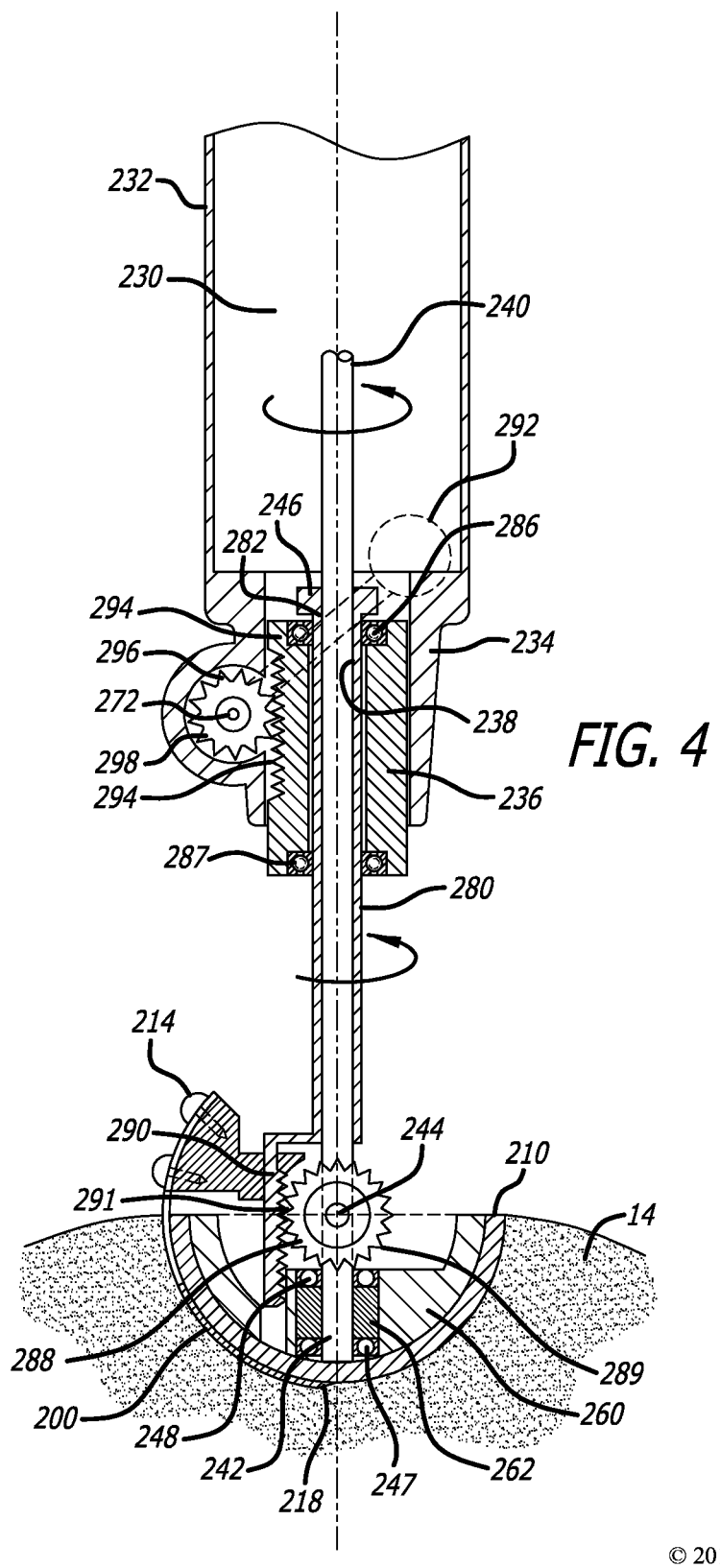
FIG. 4 is a side, partially sectioned view of applicant's acetabular cup extraction tool shown in FIG. 3. The blade in this figure has pivoted to another position than the blade shown in FIG. 3.
Figure 5:
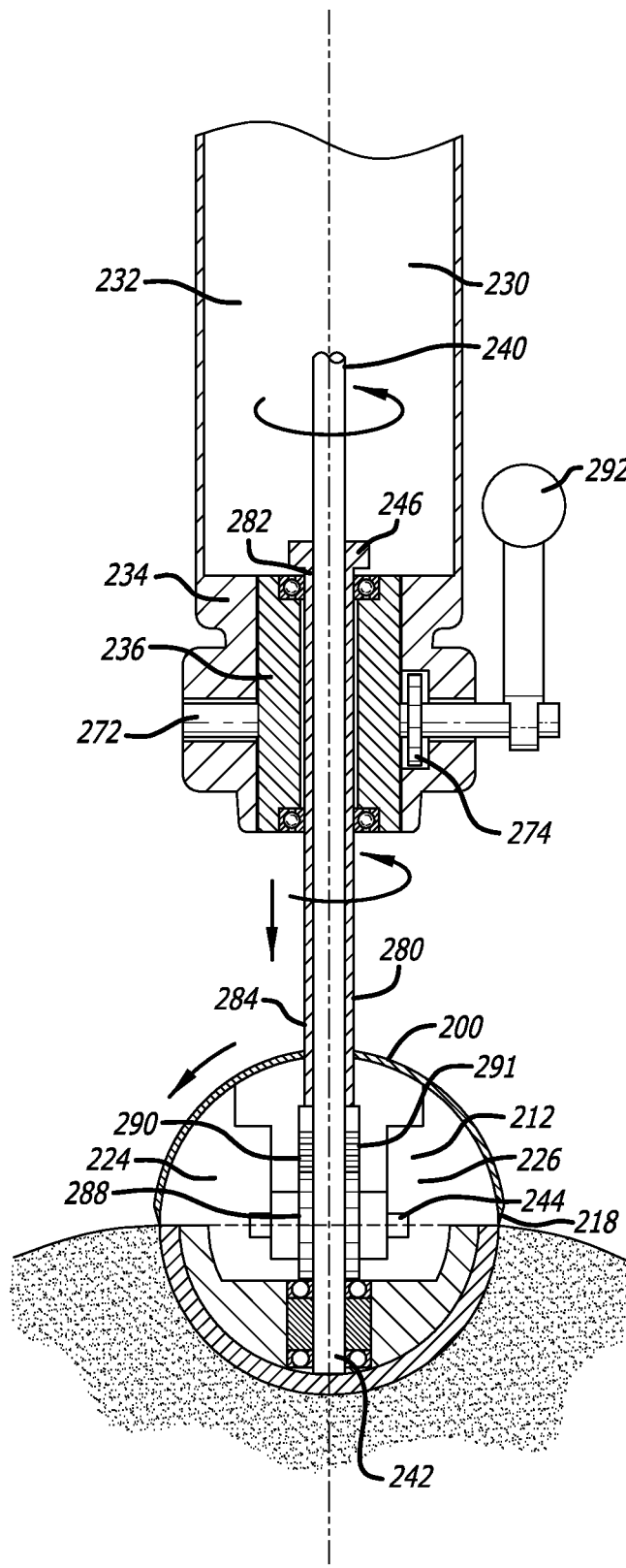
FIG. 5 is a front, partially sectioned view of the FIG. 3 version of applicant's acetabular cup extraction tool.

FIG. 5 is a front view of the FIGS. 3, 4 and 5 tool. The tool differs from the one that FIGS. 1A and 2 show. However, comparing FIG. 5's front view with FIGS. 1A and 2 may be useful for showing how blade 100 can mount to head 112. The blade includes slot 104 (FIG. 1B) through which drive shaft 140 can extend. The slot corresponds to a slot or open region in the head through which the drive shaft passes.

Distal end 142 of drive shaft 140 seats in alignment head 160. The alignment head is hemispherical to conform to the hemispherical inside surface of acetabular cup 10. Cups have different sizes for different patients, and the surgeon chooses an alignment head that conforms to each patient's acetabular cup. A roughened surface or small teeth or spikes (not shown) along the outer surface of the alignment head prevent the alignment head from pivoting within the acetabular cup during use. Fitting 162 in the alignment head supports the distal end of the drive shaft. The fitting may have at least one bearing 147 to allow rotation of the drive shaft in the fitting. FIG. 1 shows a second bearing 148. A clip below bearing 147 may prevent the distal end of the drive shaft from contacting the acetabular cup.

Blade 100 mounts on head 112, which mounts on and pivots about axle 144. (FIGS. 1A and 2). Axle 144 generally is perpendicular (horizontal in FIGS. 1A and 2) to the longitudinal axis of drive shaft 140. The axle's axis sometimes is referred to as the second axis. The head's pivoting carries blade 100 with the head. When alignment head 160 is positioned in the acetabular cup as FIGS. 1A and 2 show, cutting edge 118 of the blade is positioned at the acetabular cup/bone interface. The cutting edge also could be positioned out of contact initially so that contact only occurs after the blade begins rotating.

When the device is "on" and motor 130 rotates drive shaft 140 so that the drive shaft rotates blade 100, a linkage can pivot head 120 and the blade about the second axis, i.e., the axis of axle 144. This causes the rotating blade to move into the acetabular cup/bone interface. "Linkage" here means a device that transmits force from one component to another such as an arm or arms, a gear or gears, a friction connection, a cam or other force-transmitting component.

In FIGS. 1A and 2, the linkage comprises concentric, rotating outer sleeve 180 around drive shaft 140. The sleeve and drive shaft rotate together. The proximal end 182 of sleeve 180 extends through the tube 136, which mounts in tip 134 of housing 132. Bearings 186 and 187 allow the sleeve to rotate inside the tube.

Tube 136 can move into and out of tip 134 along inside surface 138 of the tip. Compare FIGS. 1A and 2. Clip 146 attaches to bearing 186 and the proximal end of sleeve 180. Alternatively, the sleeve could be formed with a disk at its proximal end. Thus, the clip can rotate relative to the tube with rotation of the sleeve. A mechanism, which is described below, can advance and withdraw the tube. The tube does not rotate, but as it moves distally, clip 146 and sleeve 180, which rotate, also move distally. Compare FIGS. 1A and 2. Additional bearings in motor 130 or housing 132 may support drive shaft 140 or sleeve 180 for rotation (FIGS. 1A and 2). The number, type and position of bearings are matters of choice.

Distal end 184 of sleeve 180 connects through pin 190 or other connector to one end of arm 188 (FIGS. 1A and 2). Pin 191 connects the other end of the arm to lower part 122 of head 112. The pins also may connect a complimentary, second arm (not shown) parallel to arm 188 (behind arm 188 in the drawings) to the head and sleeve. See also FIG. 9, which shows both arms for the FIG. 8 tool. The angle between a line connecting axle 144 and the longitudinal axis of drive shaft 140 may be about 40°. Because the arms are angled to the longitudinal axis of the sleeve, distal movement of the sleeve and arms, i.e., movement toward the acetabular cup, causes head 112 to pivot counter-clockwise (direction of the arrow in FIG. 1A) about the axis of axle 144. That pivoting urges cutting edge 118 of blade 100 into the acetabular cup/hipbone interface.

A driver can move tube 136 and sleeve 180 through a mechanical connection, motor, solenoid, pneumatic or hydraulic actuator or other device. FIGS. 1A and 2 show a mechanical connection. The tube 136 has a series of teeth 194. Wheel 196, which mounts on shaft 172, has outer teeth 198 that engage the tube's teeth. Teeth 194 and 198 are show schematically. They could be spur, helical or other gear teeth made to engage each other. By rear-ranging the axis of the wheel, worm or bevel gears also could be used. The wheel also could engage the tube through a friction connection, other secure drive or other type of transmission. If gears are used, depending on the type of gears, one can choose the diameter of wheel 196 and thus its number of teeth to control the leverage from the wheel against the tube 136 and sleeve 180.

Handle 192 attaches to wheel 196 (FIGS. 1A and 2). The handle's length also affects the leverage. When a surgeon pivots the handle clockwise in the direction of the arrow from the FIG. 1A position to the FIG. 2 position, wheel 196 also rotates clockwise on shaft 172. Teeth 198 on the wheel urge teeth 194 on tube 136 distally (downward in FIG. 1A), which drives the tube 136 and sleeve 180 downward. The sleeve drives arm 188 toward head 122 causing the head to pivot counterclockwise. Compare FIGS. 1A and 2. Head rotation carries blade 100 counterclockwise. Therefore, cutting edge 118 of blade 100 travels along the acetabular cup/bone interface. Because motor 130 rotates drive shaft 140, which rotates head 112, blade 100 on the head rotates about the drive shaft's longitudinal axis, the blade's cutting edge cuts along the interface as the blade pivots on with the head. Handle 192 also may have a controller operably connected to motor 130 for controlling the drive shaft's speed of rotation.

Note that as sleeve 180 moves longitudinally and rotates with drive shaft 140, the drive shaft does not move longitudinally. Thus, applicant's tool provides means for moving the sleeve relative to the drive shaft when the two components rotate together.

The design of the linkage can prevent the blade from rotating beyond its FIG. 2 position. For example, the length of the toothed section on tube 136 limits the longitudinal movement of the tube and sleeve. Fasteners 114 that hold the blade to the head also can act as a stop as head 112 and blade 100 reach the FIG. 2 position. A clip on fitting 162 also could block longitudinal movement of the drive shaft. In addition, the drive shaft could have a smaller diameter in the fitting. Thus, the fitting could block the wider diameter portion from moving distally. FIG. 11 also has structure for limiting pivoting of the head. That structure is discussed with the explanation of the figure.

After rotating blade 100 pivots to the FIG. 2 position, the acetabular cup should come loose from the hipbone. The surgeon might have to remove additional tissue that would prevent an immediate removal of the acetabular cup, however. After the blade completes its cutting, the surgeon returns handle 192 to the FIG. 1A position. When the surgeon is not urging the handle, a coil or other spring (not shown) around wheel 196 can urge the handle and wheel to the FIG. 1A position. See spring 274 in FIG. 5 as an example.

Instead of using a coil spring around the wheel or around the shaft on which wheel 196 mounts to return handle 192 and sleeve 180 to the FIG. 1A positions, the device could incorporate one or more springs or other elastic members attached to other locations on the mechanism. In addition, an electrically operated device such as a solenoid or motor could return the handle, sleeve and blade 100 to the FIG. 1A position. Such an electrically operated device also could advance the handle, sleeve and blade toward the FIG. 2 position.

The linkage in FIGS. 3, 4 and 5 includes a gear drive, which pivots head 212 and blade 200. The blade and head in these drawings may be similar to the blade and head in FIGS. 1A, 1B and 2.

Motor 230 or other motive device within housing 232 (FIGS. 3, 4 and 5) rotates drive shaft 240 about a first axis, the shaft's longitudinal axis. Drive shaft 240 may be fixed to the motor, or it may connect to a spindle that is part of the motor. Other drawings show connections between the spindle and the drive shaft that tools shown in all drawings use.

Distal end 242 of drive shaft 240 seats in hemispherical alignment head 260 (FIGS. 3, 4 and 5). The outside of the alignment head conforms to the inside hemispherical surface of acetabular cup 210. The size of the alignment head that a surgeon chooses conforms to the size of the acetabular cup. A roughened surface, small teeth or spikes (not shown) along the alignment head's outer surface holds the alignment head in one position. Fitting 262 in the alignment head supports the distal end of the drive shaft. The fitting may have a clip or stop that prevents the end of the drive shaft from projecting into the acetabular cup. Bearings 247 and 248 at the fitting's ends allow the drive shaft to rotate relative to alignment head 260 through rotation of motor 230. Additional bearings in motor 230 or housing 232 may support drive shaft 240 and other components for rotation. The number, type and position of bearings are matters of choice.

Axle 244 extends through drive shaft 240 above the drive shaft's distal end 242 and through part of head 212 (FIGS. 3, 4 and 5). The head may straddle the drive shaft in an arrangement similar to that shown in FIG. 5. As FIG. 5 shows, the axle's longitudinal axis (left to right in FIG. 5), the "second axis," which is perpendicular to the "first axis," i.e., the longitudinal axis of the drive shaft. Thus, blade 200 can pivot with the head about the second axis as motor 230 rotates the drive shaft, blade and head about the first axis. When alignment head 260 is positioned in the acetabular cup as FIGS. 3, 4 and 5 show, the blade's sharp cutting edge 218 is at the acetabular cup/bone interface.

The linkage in FIGS. 3, 4 and 5 comprises a rotating sleeve 280, which is concentric and around drive shaft 240. The sleeve and drive shaft rotate together. The sleeve's proximal end 282 extends through tip 234 and tube 236 of housing 232. Tube 236 can move into and out of tip 234 along the tip's inside surface. Bearings 286 and 287 allow the sleeve to rotate inside the tube. Clip 246 attaches to the bearing 286 and to the proximal end of sleeve 280. Instead of a clip, the sleeve could have a disk integral with the rest of the sleeve. Thus, the clip can rotate relative to the tube as the sleeve rotates. A mechanism, which is described below, can advance the tube, and the clip and sleeve move distally with the tube's distal movement. However, the tube does not rotate.

Outer teeth 298 on wheel 296 engage teeth 294 on tube 236. The wheel and handle 292 attaches to shaft 272 although the wheel and handle may be a single piece. The wheel rotates clockwise as the surgeon pivots the handle clockwise. The wheel's teeth drive the tube's teeth distally, which drives the tube and sleeve 280 distally (downward in FIGS. 3, 4 and 5) toward the acetabular cup.

Distal end 284 of sleeve 280 includes an extension 290 that includes teeth 291. Wheel 288 is attached to or is integral with head 212. Teeth 291 on the toothed extension engage teeth 289 on wheel 288. Downward or distal movement (FIGS. 3, 4 and 5) of sleeve 280 causes the teeth on the toothed extension to drive the toothed wheel counterclockwise about the axis of axle 244 between the FIGS. 3 and 4 positions. This movement causes head 212 to pivot counterclockwise about the axis of axle 244, which in turn carries blade 200 with the head. The pivoting causes the blade's cutting edge 218 to move along the acetabular cup/hipbone interface. Because the blade rotates about the longitudinal axis of drive 240 as the blade pivots about the axis of axle 244, the cutting edge cuts along the interface. In FIGS. 3 and 4, the extension may be offset from the more proximal portion of the sleeve. However, the sleeve's and wheel's diameters determine if extension 290 is offset from the rest of the sleeve.

After head 212 and blade 200 pivots approximately 90° from the FIG. 3 to the FIG. 4 position as the motor rotates the head and blade, the hipbone should release acetabular cup. When the cup become loose, the surgeon returns handle 292 to the FIG. 3 position. Spring 274 (FIG. 5) around wheel 296 can urge the handle and wheel to the FIG. 3 position. Wheel 288 also could be spring-loaded. After the blade is withdrawn, the surgeon removes the device from the acetabular cup.

Figure 6:
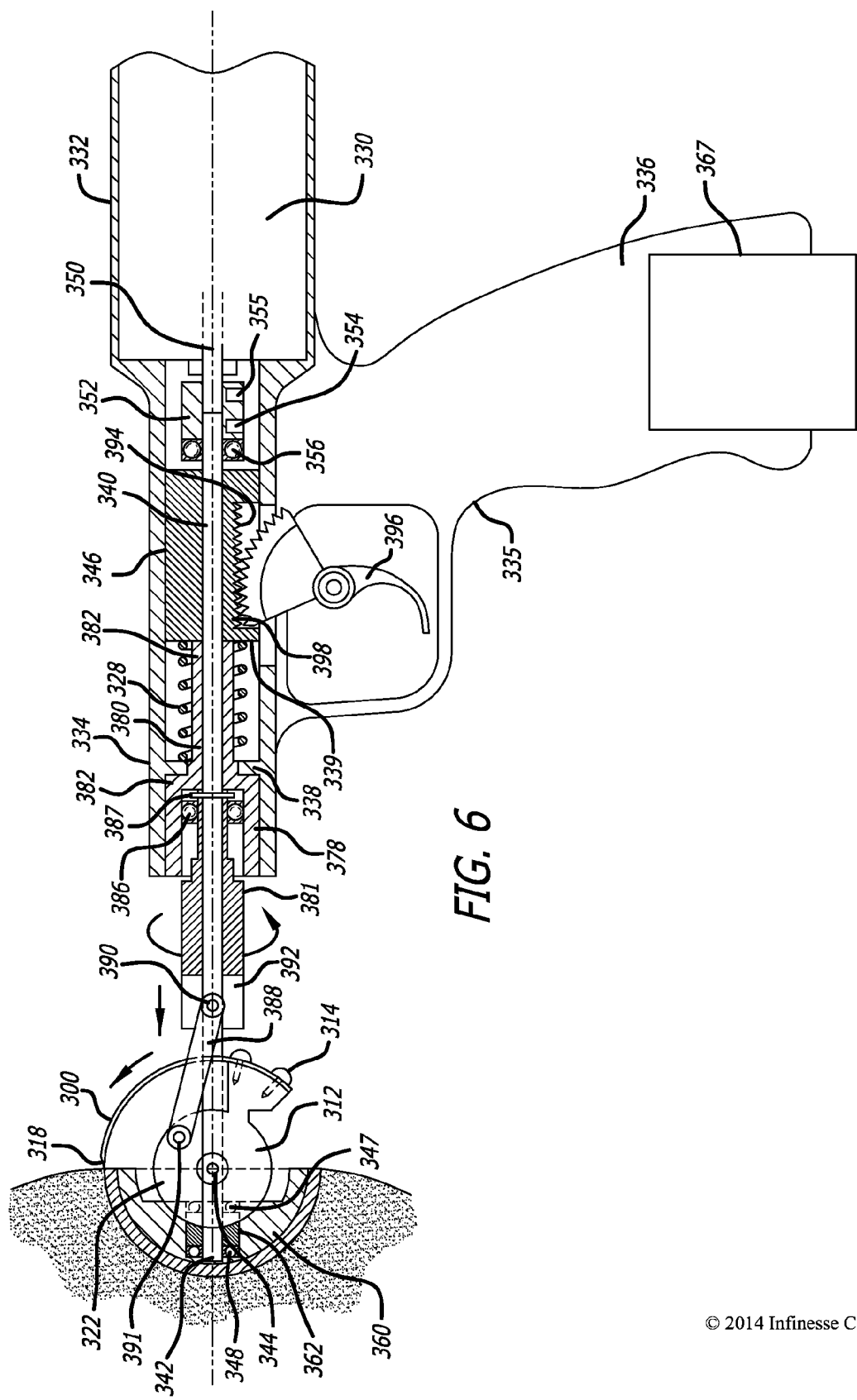
FIG. 6 is a side, partially sectioned view of a different version of applicant's acetabular cup extraction tool.
Figure 7:
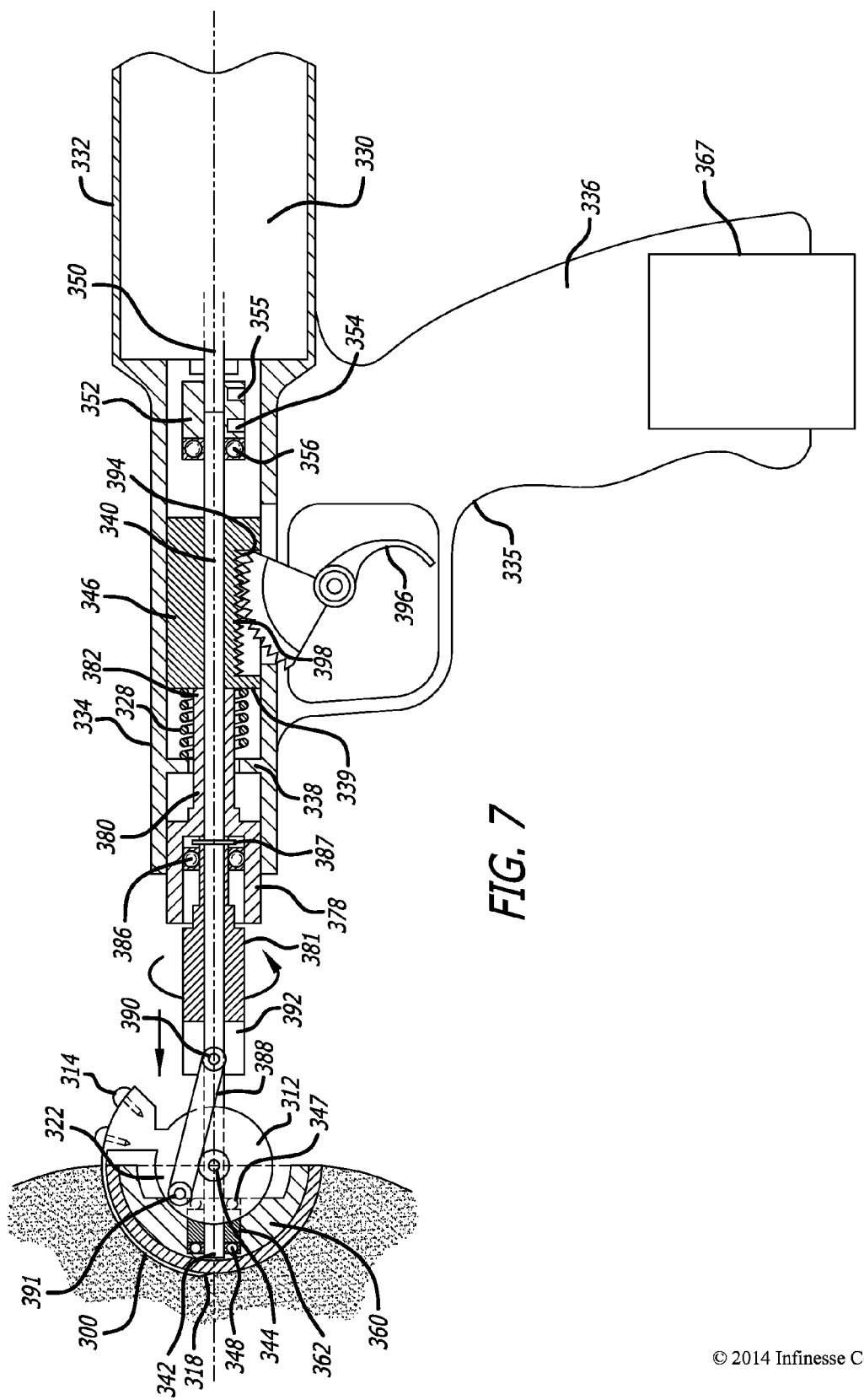
FIG. 7 is a side, partially sectioned view of applicant's acetabular cup extraction tool shown in FIG. 6. The blade in this figure has pivoted to another position than the blade shown in FIG. 6.

Housing 332 in FIGS. 6 and 7 includes handle 366 that makes the housing pistol-shaped. Surgeons may find pistol shapes easier to use. The handle may have indentations such as indentation 335 so that the handle resembles some pistol handles.

Motor 330 or other motive device within housing 332 rotates drive shaft 340 about its longitudinal axis. The handle may have a cavity for receiving a swappable battery pack 367. The tool could use other power sources or be operated pneumatically or hydraulically, but it uses battery power in FIGS. 6 and 7.

At the other end of the tool, fasteners 314 or other attachments secure blade 300 to head 312. The blade and head in FIGS. 6 and 7 may be similar to the blade and head in other figures in that blade 300 includes a sharp, possibly serrated cutting edge 318 (FIGS. 6 and 7) at its distal end. The blade also may have special teeth as described with the tool shown in FIG. 11.

Drive shaft 340 may be fixed to or removable from motor 330. The drive shaft in FIGS. 6 and 7 connects to short spindle 350. The shafts' respective ends can have shapes that engage each other, or the ends can be flat. In FIGS. 6 and 7, the distal end of the spindle and the proximal end of the drive shaft extend into the center bore of coupler 352. The portions of the spindle and drive shaft that mount within the coupler may have non-circular cross-sections (e.g., hexagonal) that mate with a similar shape cross section of the coupler's bore. Therefore, the drive shaft and spindle will not rotate relative to the bore. Setscrews (not shown) or other fasteners extend into threaded openings 354 and 355 of the coupler to engage the drive shaft and spindle respectively. The drawing shows only two threaded openings, but additional openings can be spaced 120° or another distance apart radially around the coupler. As the motor rotates the spindle, the coupler also rotates and transfers the motor's rotation to the drive shaft.

The mechanism in FIGS. 6 and 7 for pivoting head 312 and for driving blade 330 into the acetabular cup/hipbone interface includes axle 344. The axle extends through drive shaft 340 above its distal end 342 and through the head. The head may straddle the drive shaft in an arrangement similar to that shown in FIG. 5. The axis of axle 344, the "second axis" generally is perpendicular to the longitudinal axis of drive shaft 340, the "first axis."

Distal end 342 of drive shaft 340 seats in fitting 362 in alignment head 360 (FIGS. 6 and 7). Bearings 347 and 348 allow motor 330 to rotate the drive shaft to rotate in the fitting. The fitting may have structure for positioning the drive shaft in the fitting so that the drive shaft does not extend out of the fitting into the acetabular cup. The tool shown in FIGS. 6 and 7 can use previously described structure, for positing and holding the alignment head in the acetabular cup.

Head 312, which mounts on axle 344 (FIGS. 6 and 7), pivots about the axle's axis, i.e., the second axis. Drive shaft 340 can rotate about its longitudinal axis, i.e., the first axis, as the head pivots about the second axis. Blade 300, which is secured to the head, pivots with the head. Cutting edge 318 of the blade is positioned at the acetabular cup/bone interface when head 312 is at or in the acetabular cup.

A linkage pivots head 312 and blade 300 about axle 344 into the acetabular cup/bone interface as drive shaft 340 rotates the head and blade. The linkage may comprise a concentric, sleeve 380 around the drive shaft and a sleeve extender 381 extending distally from the sleeve. The sleeve, sleeve extender and drive shaft rotate together. Although the sleeve and sleeve extender can be separate components especially when they are manufactured individually, they can be considered as one element because they can move together. Thus, in some instances, saying that the sleeve moves may mean that the sleeve and sleeve extender move.

In FIGS. 6 and 7, the distal end of sleeve 380 forms cup 378, which is open distally. The proximal end of sleeve extender 381 extends into the cup. Bearing 386, which is secured by clip 387, guides the sleeve extender longitudinally relative to sleeve cup 378.

The tool in FIGS. 6 and 7 includes moving assembly 346, which has a series of outer teeth 394. Trigger 396 has mating teeth 398 that engage the moving assembly's teeth. Distal end 399 of the moving assembly is against the proximal end 382 of sleeve 380. When the surgeon pulls the trigger, teeth 398 on the trigger drive the moving assembly's teeth distally (to the left in FIGS. 6 and 7). Distal travel of the moving assembly urges sleeve 380 and sleeve extender 381 in the same direction, which is longitudinally relative to the drive shaft 340.

In FIGS. 6 and 7, the distal end 392 of sleeve extender 381 has an open center through which drive shaft 340 extends. Pin 390 attaches arm 388 to the distal end of the sleeve extender. A pin also attaches a second arm (not shown) to the sleeve extender. The pins are out of contact with the drive shaft; they attach only to the sleeve extender. Consequently, the sleeve extender can move longitudinally without applying force longitudinally on the drive shaft. Pin 391 attaches the other end of the arm 388 and the second arm to head 312.

When moving assembly 346, sleeve 380 and sleeve extender 381 move distally as trigger 396 pivots counterclockwise, pin 390 on the sleeve extender drives pin 390 and arm 388 distally. Because pin 391, which attaches the other end of the arm to head 312, is spaced from the longitudinal axis of the drive shaft, sleeve and sleeve extender, the arm pivots the head counter-clockwise (in the arrow's direction in FIGS. 6 and 7) about axle 344. The head, which is rotating from motor rotation acting on drive shaft 340, carries blade 300 with the head. Thus, pivoting the head urges cutting edge 318 of the blade into the acetabular cup/hipbone interface. Rotation of the blade about the longitudinal axis of drive shaft 340 while the blade is pivoting into the interface allows the blade's cutting edge to cut along the interface.

After blade 300 reaches the FIG. 7 position, the loosened acetabular cup can be removed from the hipbone. The surgeon releases trigger 396 so that it returns to the FIGS. 6 and 7 position under urging from spring 328. The spring in FIGS. 6 and 7 surrounds sleeve 380. The distal end of the spring pushes against stop 338, which extends inward from near distal end 334 of housing 332. The spring also pushes against moving assembly 346. The spring, therefore, urges moving assembly 346 proximally (to the right in FIGS. 6 and 7), and the sleeve and sleeve extender follows.

The length of the tool from the end (right side in FIGS. 6 and 7) of the housing to the distal end of the drive shaft (left side) may be about 14 in (≈36 cm).

Instead of the mechanical connections shown in FIGS. 6 and 7 and other drawings, an electrical mechanism such as a stepper motor or solenoid or a pneumatic or hydraulic actuator could position the sleeve or drive the head and blade directly. Accordingly, trigger 398 could connect to an electrical switch to control a motor, solenoid or other actuator. The tool also could have a separate control that allows the surgeon to activate motor 330 irrespective of the trigger position. The separate control also could allow the surgeon to adjust the rotational speed. See also FIG. 8, which shows such a separate control.

Figure 8:
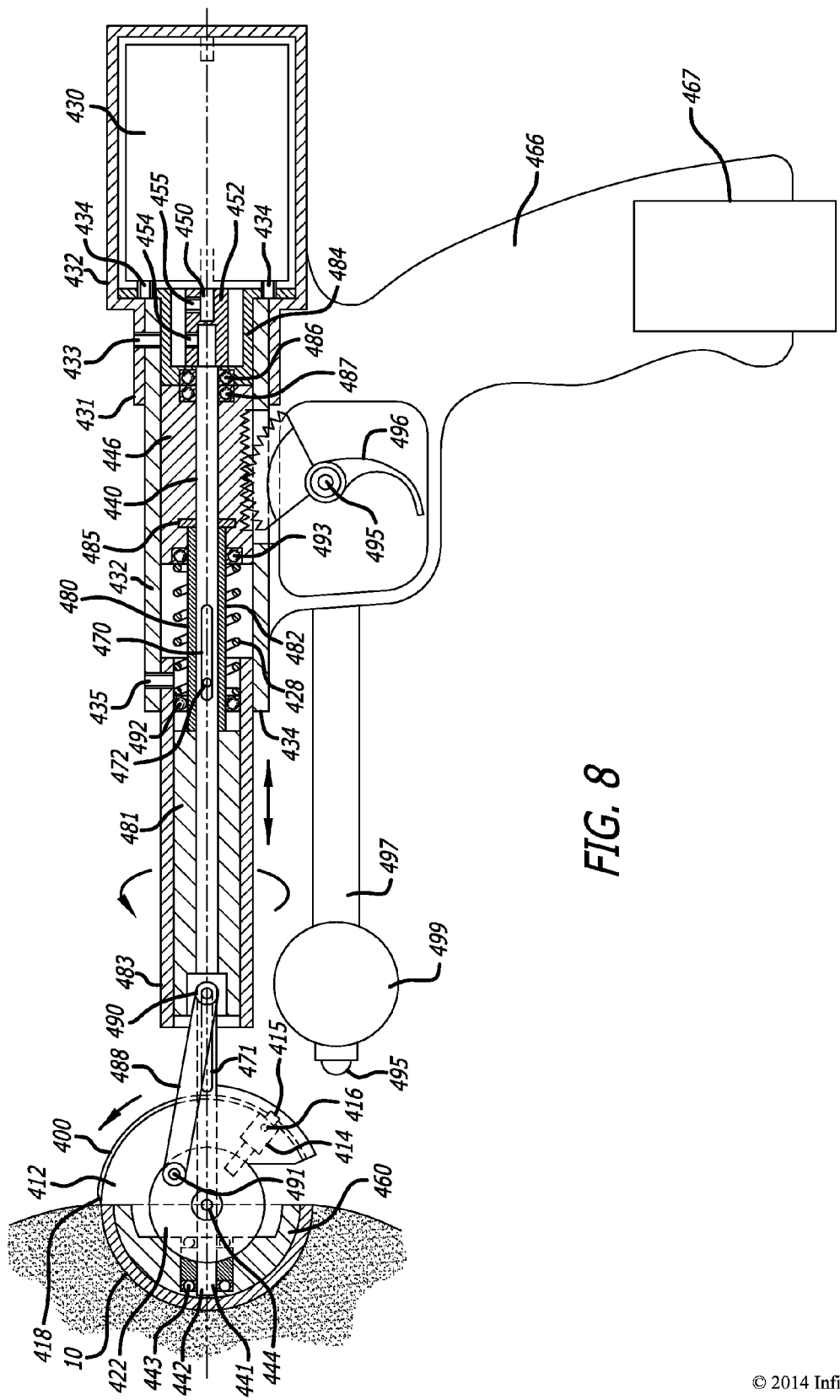
FIG. 8 is a side, partially sectioned view of another version of applicant's acetabular cup extraction tool.

Housing 432 in FIG. 8 includes handle 466 so that the tool is pistol-shaped. Motor or other motive device 430 within housing 432 rotates spindle 450 about its longitudinal axis. The handle also receives swappable battery pack 467 or other power source.

Housing 432 that FIG. 8 shows includes a removable motor cover 431. Fasteners such as setscrews (not shown) in one or more openings 433 secure the cover to the rest of the housing. Setscrews (not shown) in openings 434 secure the motor to the housing. Drive shaft 440 may be attached permanently or removably to the motor. In FIG. 8, spindle 450 extends distally (to the left) into the open center of shaft coupler 452. The drive shaft extends into the coupler from the coupler's other end. The respective ends of the drive shaft and spindle can have shapes that engage each other. Otherwise, the shaft ends can be flat. Setscrews (not shown) or other fasteners extend into threaded openings 454 and 455 in the coupler to engage the drive shaft and spindle respectively. FIG. 8 shows only two threaded openings, but additional radially spaced setscrews (e.g., 120° apart) can be located around the shaft coupler. Because the coupler secures the spindle and drive shaft together, rotation of the spindle causes drive shaft 440 to rotate. As with the tools shown in other drawings, the coupler may have a non-circular cross-section, the portions of the spindle and drive shaft that extend into the coupler may have similar cross-sections. Therefore, the spindle and drive shaft do not rotate relative to the coupler. Instead, they and the coupler rotate together.

At the tool's other end (left in FIG. 8 (also shown in FIG. 9)), head 412 mounts on axle 444. The axle's axis (the "second axis) extends through drive shaft 440 at its longitudinal axis ("first axis"). The head acts as a hub assembly fixture that integrates several components. Quick-release fasteners 414 or other attachments secure blade 400 to head 412. Quick release fasteners for the blades in other figures were mentioned with less detail.

The fasteners in FIG. 8 include a spring-loaded plunger 415, which extends outward from base 416 of the fastener into openings 402 in blade 400. See FIG. 10. Blade 400 and head 412 in FIG. 8 may be similar to the blade and head in other figures. The blade includes sharp, possibly serrated, cutting edge 418 at its distal end. In addition, the blade may have grooves 406 (FIG. 10), other indentations or raised areas to channel debris away and allow water or other fluid to irrigate the surgery.

Blade 400 may be hemispherical, or it may be a segment of a sphere. It should be long enough to travel entirely along the outside of the acetabular cup when the blade is inserted into the acetabular cup-hipbone interface as the motor rotates the blade.

Axle 444 is perpendicular to and extends through drive shaft 440 above distal end 442 of the drive shaft. The axle also extends through head 412. Head 412 may straddle drive shaft 440. See FIG. 9. The blade has an open area 404, and the head has an open area 408 (FIGS. 9 and 10) to accommodate the drive shaft.

Figure 9:
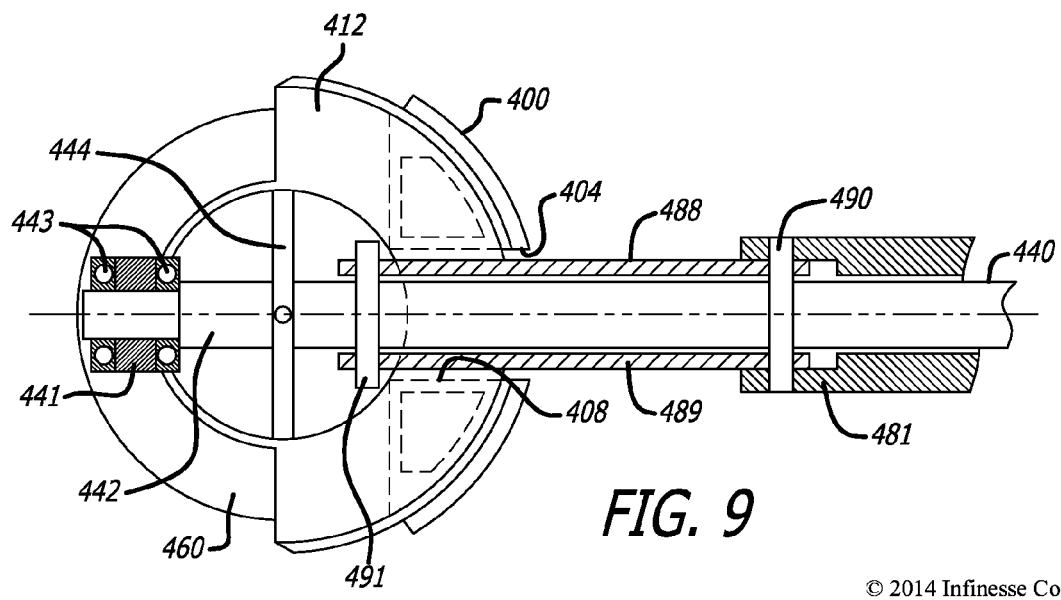
FIG. 9 is a front, partially sectioned view of the distal end of applicant's acetabular cup extraction tool shown in FIG. 8.

Distal end 442 of drive shaft 440 seats in fitting 441 of hemispherical alignment head 460 (FIGS. 8 and 9). Bearings 443 in the alignment head receive the drive shaft and facilitate rotation of the drive shaft in the alignment head. The distal end of the drive shaft may have a narrower diameter than the rest of the drive shaft as FIG. 9 shows. The fitting and bearing accommodate the smaller diameter. The wider diameter portion of the drive shaft cannot pass through the fitting and bearings. That arrangement prevents the drive shaft from direct contact with the acetabular cup. Other arrangements could position the distal end of the drive shaft in the fitting and out of contact with the acetabular cup.

Alignment head 460 is hemispherical to conform to the inside surface of acetabular cup 10. The alignment head may have structure such as a roughened surface, teeth or spikes to hold its position in the acetabular cup after the surgeon positions the alignment head in the cup. Different diameter alignment heads allow the tool to interact with different diameter acetabular cups.

Because head 412 mounts on axle 444 in FIGS. 8 and 9, and the axle also extends through drive shaft 440, the head can pivot about the axle's axis as drive shaft 440 rotates about its longitudinal axis. Blade 400, which is secured to the head, pivots as the head pivots. The blade also rotates about the drive shaft's longitudinal axis as the motor rotates the drive shaft. The mechanism that pivots the head is described below. As FIG. 8 shows, the blade's cutting edge 418 is positioned at the acetabular cup/bone interface when head 412 and alignment head 460 is in the acetabular cup.

During the tool's operation, a linkage pivots head 412 and blade 400 about axle 444 into the acetabular cup/bone interface. The linkage comprises sleeve 480, which rotates with motor-driven rotation of drive shaft 440. Sleeve extender 481, which also is around the drive shaft, extends distally from the sleeve. The sleeve and sleeve extender may be separate components, or they may be formed as a single component. The sleeve, sleeve extender and drive shaft rotate together. A protective shroud 483 may cover the sleeve extender. In FIG. 8, the shroud also covers the distal end of the sleeve. The shroud can connect to the distal end of housing 432 through a setscrew in opening 435. Multiple setscrews could be used. The setscrew allows the shroud to be removable for access to the sleeve extender. The shroud and the distal end of the housing could be a single component.

To facilitate motor-driven rotation of drive shaft 440, bearings such as bearing 486, which mounts in fitting 484 in the housing, and bearing 487, which mounts in moving assembly 446, support the drive shaft.

FIG. 8 shows a mechanical connection that moves sleeve 480 along a first axis, the longitudinal axis of drive shaft 440. A motor or other device can replace or augment the mechanical connection. In FIG. 8, the mechanical connection includes moving assembly 446, which includes a series of teeth 494. The moving assembly is mounted to slide without rotating along the inside of housing cover 432. Cooperative guides on the housing and the moving assembly (not shown) can maintain the moving assembly in a correct orientation as the moving assembly slides. Trigger 496, which pivots on shaft 495, has mating teeth 498 that engage the moving assembly's teeth. Thus, pulling the trigger, i.e., rotating it counterclockwise, causes the teeth on the trigger to urge the teeth on the moving assembly distally (to the left in FIG. 8). Consequently, the moving assembly moves distally.

Ring clip 485 seats near the distal end 447 of moving assembly 446. The clip is in contact with proximal end 482 of sleeve 480. Thus, the ring clip couples the moving assembly to the sleeve for longitudinal movement but not for rotation. Bearings 492 and 493 support sleeve rotation relative to the moving assembly. The distal end of the sleeve contacts the proximal end of the sleeve extender. Therefore, when the surgeon pulls trigger 496, teeth 498 on the trigger drive the moving assembly's teeth distally (to the left in FIG. 8). Consequently, the sleeve and sleeve extender 481 move distally.

Pin 490 attaches arms 488 and 489 to sleeve extender 481, and pin 491 attaches the arms to head 412. See FIG. 9, which shows both arms, but only pin 488 is visible in FIG. 8. Sleeve 480 and sleeve extender 481 can move longitudinally relative to drive shaft 440 along the common axis of rotation of the sleeve, sleeve extender and drive shaft. The drive shaft has two slots, proximal slot 470 and distal slot 471 (FIG. 8). Pin 472 on the sleeve extends through proximal slot 470 in the drive shaft. That slot also could be positioned such that the pin extending through the slot could be in sleeve extender 481. Pin 490, which connects arms 488 and 489 at sleeve extender 481, extends through distal slot 471 and through the drive shaft where it engages the sleeve extender. See FIG. 9.

When the surgeon pulls trigger 496, moving assembly 446 urges sleeve 480 and sleeve extender 481 distally, but drive shaft 440 only can rotate. It does not move longitudinally. Because arms 488 and 489 connect to the head away from the sleeve's longitudinal axis, distal movement of the arms causes the head to pivot counterclockwise in the arrow's direction in FIG. 8 about the axis of axle 444. The head carries blade 400 with it such that the pivoting of the head urges cutting edge 418 of the blade into the acetabular cup/hipbone interface. Motor-driven rotation of the blade about the longitudinal axis of the drive shaft while the blade is pivoting into the interface causes the blade's cutting edge to cut along the interface.

The tool shown in FIG. 8 also may include guide 497 for the surgeon's second hand. Such a guide may help the surgeon stabilize the tool. Speed control button 495 or other controller allows the surgeon to control the powered rotational speed of drive shaft 440, head 412 and blade 400 about the drive shaft's axis of rotation. Instead of a speed controller button 495, ball 499 at the end of the guide may rotate on the guide for use as a speed controller.

After the blade in FIG. 8 pivots about 90°, the acetabular cup should come loose from the hipbone. The surgeon releases trigger 496 so that it returns to the FIG. 8 position under urging from coil spring 428. The distal end of the spring pushes against bearing 492, and the proximal end of the spring pushes against bearing 493 at moving assembly 446. When the surgeon releases the trigger fully or partially, the proximal end of the spring urges the moving assembly proximally (to the right in FIG. 8). As a result, sleeve 480 also moves proximally, which causes arms 488 and 489 to urge head 412 clockwise in FIG. 8. That movement of the head carries the blade back to the FIG. 8 position.

Housing 532, which FIG. 11 shows, also includes pistol-shaped handle 536. Motor or other motive device 530 at the proximal end of the housing (right side of FIG. 11) rotates spindle 550 about its longitudinal or first axis (horizontal in FIG. 11). Opening 568 in the handle receives battery pack 567 or other power source. The battery pack is designed for easy insertion and removal from the handle's opening to allow replacement of a discharged battery with a charged one.

Housing 532 may include removable cover 531. Setscrews 537 and 538 secure the cover to fitting 548 and protective shroud 583. Those latter parts remain stationary when the device is in use. Removing the cover and shroud allows access to the tool's internal parts.

Drive shaft 540 may be attached to the motor, or it may be a continuation of a long spindle. In FIG. 11, spindle 550 and drive shaft 540 are separate. The spindle extends distally (to the left in FIG. 11) into a center bore of shaft coupler 552. The drive shaft extends into the coupler from the coupler's other end. The respective ends of the drive shaft and spindle can be flat or have shapes that engage each other. Setscrews 554 and 555 or other fasteners extend into threaded openings in the coupler to engage the drive shaft and spindle respectively. FIG. 11 shows only two setscrews, but the tool could add radially, spaced setscrews around the shaft coupler. Fitting 546 may also have openings for access to the coupler and its setscrews. The ends of the spindle and drive shaft that extend into the coupler may be shaped to mate with a corresponding shape inside the coupler to prevent the spindle and drive shaft from rotating within the coupler. Thus, the spindle and drive shaft rotate together as the motor rotates because they attach to the coupler.

Blade 500 mounts on head 512 near the distal end of the tool (left side in FIG. 11). As explained in more detail below, the tool has a mechanism for pivoting the blade along the acetabular cup/hipbone interface as the blade rotates from powered rotation of drive shaft 540 about the shaft's longitudinal axis. The blade may be a standard size or it may be custom for different diameter acetabular cups. However, the inside of the acetabular cup is hemispherical irrespective of its diameter Quick-release fasteners 514 or other attachments secure blade 500 to head 512 near the tool's distal end. The fasteners includes a spring-loaded plunger 515, which extends outward from base 516 of the fastener into openings 502 in blade 500. See FIG. 12. Blade 500 and head 512 in FIG. 11 may be similar to the blade and head in other figures. The blade includes sharp, possibly serrated, cutting edge 518 at its distal end. In addition, the blade may have grooves 406 (FIG. 10) or other indentations or raised areas to channel debris away and allow water or other fluid to irrigate the surgery.

Figure 13:
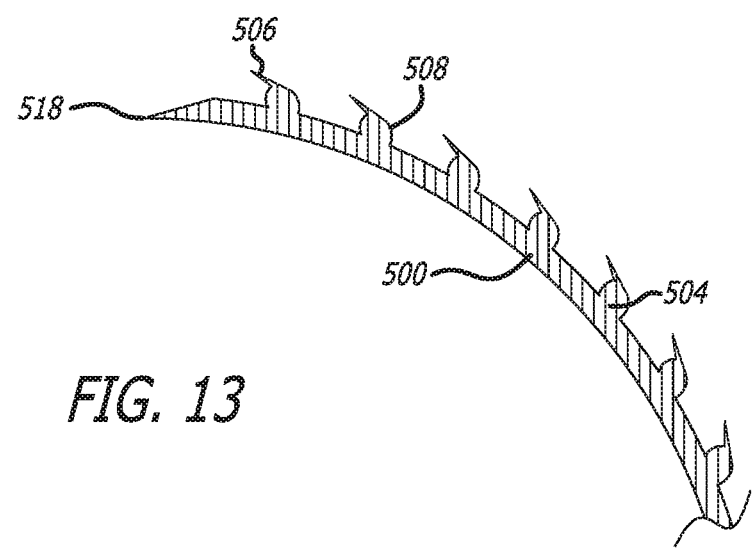
FIG. 13 is a side sectional view of teeth that could be used on the blade.

Blade 500 also may have teeth 504. See FIG. 13. Tips 506 of the teeth are angled outward. The teeth also have rounded bottom edges 508. The design makes cutting into the patient's metal acetabular cup surface less likely. Avoiding cutting into the acetabular cup avoids generating metal debris in the patient.

The mechanism in FIG. 11 that pivots blade 500 into the acetabular cup/hipbone interface pivots about or with axle 544. The axis of the axle is perpendicular to and extends through the axis of drive shaft 540 above its distal end 542 and partially or fully through head 512. The head may straddle drive shaft 540. The blade in FIG. 10 has an open area and the head in FIG. 11, which is similar to the head in FIG. 10, has an open area (see area 408 in FIG. 9) to accommodate the drive shaft.

Hemispherical alignment head 560 conforms to the acetabular cup's inner hemispherical surface. See FIGS. 11 and 12. Alignment heads may be standard sized or they may be custom sized for different diameter acetabular cups. They also may be disposable. Distal end 542 of drive shaft 540 seats in fitting 541 in the alignment head. (FIGS. 8 and 9). Bearing 543 in the alignment head's fitting receives the drive shaft and facilitate rotation of the drive shaft in the alignment. C-clip 539 or other fastener in the fitting prevents the drive shaft from extending out of the fitting and into the acetabular cup. Alternatively, the distal end of the drive shaft may have a smaller diameter in the fitting. The fitting or the bearing blocks the larger diameter portion of the drive shaft from passing through the fitting.

The outer surface of alignment head 560 may have a roughened surface or small teeth or spikes (not shown) to prevent the alignment head from pivoting within the acetabular cup. After positioning the alignment head in the acetabular cup, the surgeon pushes on the tool to achieve a press fit. The roughened surface or teeth should hold the alignment head in one position with the drive shaft at the center of the acetabular cup Axle 544 about which head 512 can pivot may extend through drive shaft 540. Thus, as the motor-driven drive shaft rotates about it longitudinal axis (horizontal in FIG. 11), the head can rotate about that axis. Blade 500, which is secured to the head, pivots as the head pivots and rotates as the drive shaft rotates. The mechanism that pivots the head is described below. As FIG. 11 shows, the blade's cutting edge 518 is positioned at the acetabular cup/bone interface when head 512 and alignment head 560 is in the acetabular cup.

In FIG. 11, the linkage that pivots head 512 comprises rotating sleeve 580 concentric with drive shaft 540 and sleeve extender 581 around the drive shaft extending distally from the sleeve. The sleeve and sleeve extender are integral in FIG. 11, but they could be separate components. The sleeve, sleeve extender and drive shaft rotate together.

Protective shroud 583 may cover sleeve 580 as FIG. 11 shows. The shroud does not extend over sleeve extender 581 in FIG. 11, but it could be designed to do so. Setscrews 537 secure the shroud to cover 531. The setscrews allow one to remove the shroud for access to the tool's internal parts. In addition, protector 578 (FIGS. 11 and 12) may slide onto the distal end of the shroud. The protector may include curved shield 579. The protector and its shield block debris from reaching the tool's internal mechanism and may prevent some debris from contacting the surgeon or surgical staff.

A mechanical connection moves sleeve 580 longitudinally (horizontally in FIG. 11) relative to drive shaft 540. A motor or other device can replace or augment the mechanical connection. Moving assembly 546, which is mounted to slide without rotating along the inside of housing cover 531, includes a series of teeth 594. Cooperative guides on the housing cover and the moving assembly (not shown) can maintain the moving assembly in a correct orientation as the moving assembly slides. Trigger 596, which pivots on shaft 595, has mating teeth 598 that engage the moving assembly's teeth. Thus, as the surgeon depresses plunger 593, the trigger rotates counterclockwise about shaft 595. The teeth on the trigger urge the teeth on the moving assembly distally (to the left in FIG. 11) so that the moving assembly moves distally. Distal movement of the moving assembly (to the left in FIG. 11) drives sleeve 580 and sleeve extender 581 distally. Thus, the trigger is the actuator that drives the sleeve and sleeve extender distally.

Bearing 586 in fitting 548 in the housing and bearing 587 in moving assembly 546 reduce friction as drive shaft 540 and sleeve 580 rotate. Distal end 547 of moving assembly 546 engages proximal end 582 of sleeve 580. See FIG. 11. Retainer clips 551 hold bearing 592 in place on sleeve 580. The bearing allows rotation of the sleeve relative to the moving assembly. Bearing 576, which is held by clip 577, supports the distal end of the sleeve for rotation.

Pin 590 attaches arms 588 and 589 (the latter is visible in FIG. 12) at sleeve extender 581. Pin 591 attaches the arms to head 512. Sleeve 580 can move longitudinally relative to drive shaft 540 along the common axis of rotation of the sleeve and drive shaft. Two slots, proximal slot 570 and distal slot 571 (FIG. 11), extend through the drive shaft. Pin 572, which is secured to opposite sides of the sleeve, extends through proximal slot 570 through the drive shaft. Pin 590, which connects arms 588 and 589, extends through distal slot 571 in the drive shaft. The ends of pin 590 do not contact sleeve extender. See FIG. 12. Compare pin 490, which is engaged by sleeve extender 481 in FIG. 9.

When the surgeon pulls trigger 596, teeth 598 drive moving assembly distally, which in turn drives sleeve 580 and sleeve extender 581 distally relative to drive shaft 540. Distal movement of the sleeve extender causes the sleeve extender to contact pin 590 and move the pin distally through slot 571. Consequently, the pin drives arms 588 and 589. See FIGS. 11 and 12. Because the arms connect to the head spaced from the sleeve's longitudinal axis, distal movement of the arms cause the head to pivot (counterclockwise in the arrow's direction in FIG. 11) about axle 544. The head carries blade 500 with it such that the pivoting of the head urges cutting edge 518 of the blade into the acetabular cup/hipbone interface. Rotation of the head and blade about the longitudinal axis of drive shaft 540 (first axis) while the head and blade pivot about the axis of the axle (second axis) into the interface causes the blade to cut along the interface.

Head 512 may have structure that limits its pivoting to about 90°. In FIG. 11, the head has a recessed region 513 bounded by shoulders 517 and 519. Shoulder 517 is radially about 90° from fitting 541, and the shoulder engages the fitting when the head rotates 90°. Thus, the fitting limits the head from pivoting more than 90°. Likewise, shoulder 519 engages the other side of fitting 514 when the head is in the FIG. 11 position. Therefore, the head cannot over-rotate beyond that position.

Housing 532 may have a second plunger 535, which can control other tool functions such as the speed of motor 530. Positioning plungers 593 and 535 near each other allows the surgeon to control pivoting of the blade and motor speed with two fingers.

The tool also may include adjustable handle 562 for stabilizing the surgeon's second hand and to allow that hand urge the tool toward the acetabular cup. The handle is adjustable about pivot 564. The pivot may have a lock to hold the position of the handle. Ball 565 or other shaped end may have a motor speed controller in place of or in addition to the speed controller associated with plunger 535. Sleeve grip 556 attaches the handle to the shroud 583. When the handle lock is released, the handle can slide longitudinally to allow the surgeon to position the handle. The handle and shroud may have guides for aligning the shroud and sleeve grip.

After the blade cuts through the acetabular cup/hipbone interface, the cup should come loose. The surgeon releases trigger 596 so that it returns to the FIG. 11 position under urging from coil return spring 528. The spring pushes against the proximal end of shroud 583 and the distal end of moving assembly 546. The spring urges the moving assembly proximally (to the right in FIG. 11). As a result, sleeve 580 also moves proximally, which causes arms 588 to pull head 512 clockwise (in FIG. 11). The return spring could act on other components. For example, it could urge trigger 596 clockwise, which would cause the teeth on the trigger and the moving assembly to drive the moving assembly proximately.

As with the tools shown in other drawings, the tool in FIG. 11 could replace one or more mechanical connections with an electrical mechanism such as a stepper motor or solenoid. A pneumatic or hydraulic actuator also could position sleeve 580 or drive the head and blade directly. Accordingly, trigger 598 could connect to an electrical switch to control a motor, solenoid or other actuator.

The tool in FIG. 11 (and other figures) uses no gears transfer powered rotation from the motor to e drive shaft 540 and sleeve 570. Because gears can cause vibration, noise and more complexity and cost, eliminating gears can be advantageous.

The description is illustrative, not limiting and by way of example only. Although this application shows and describes examples, those having ordinary skill in the art will find it apparent that changes, modifications or alterations may be made. Many of the examples involve specific combinations of method acts or system elements, but those acts and those elements may be combined in other ways to accomplish the same objectives.

"Plurality" means two or more. A "set" of items may include one or more of such items. The terms "comprising," "including," "carrying," "having," "containing," "involving," and the like in the written description or the claims are open-ended, i.e., each means, "including but not limited to." Only the transitional phrases "consisting of" and "consisting essentially of" are closed or semi-closed transitional phrases with respect to claims. The ordinal terms such as "first," "second," "third," etc., in the claims to modify a claim element do not by themselves connote any priority, precedence, or order of one claim element over another or the temporal order in which acts of a method are performed. Instead, they are used merely as labels to distinguish one claim element having a certain name from another element having the same name (but for use of the ordinal term). Alternatives such as "or" include any combination of the listed items.

I claim:

1. A powered device for extracting a prosthetic acetabular cup attached to a hipbone, the device comprising:
    a generally hemispherical blade having a distal end and a proximal end, the distal end having a cutting surface, and the blade having a slot extending from and through the distal end toward the proximal end of the blade;
    a drive shaft having distal and proximal ends and a first axis longitudinal with the drive shaft, the proximal end being operably connected to a motor for rotating the drive shaft about the first axis, the blade being mounted near the distal end of the drive shaft for pivoting about a second axis generally perpendicular to the first axis; and
    a linkage operably connected to the blade through the slot of the blade, the linkage pivoting the blade about the second axis such that the blade extends between the acetabular cup and the hipbone as the drive shaft rotates the blade, wherein the linkage comprises a sleeve coaxial with and extending around at least part of the drive shaft, the sleeve being movable along the first axis, the sleeve being operably connected to the blade, whereby movement of the sleeve pivots the blade about the second axis.

2. The device of claim 1, further comprising a head, the blade being mounted on the head, wherein the operable connection between the sleeve and the blade comprises at least one arm extending from the sleeve to the head, the at least one arm being angled relative to the first axis.

3. The device of claim 1, further comprising a head, the blade being mounted on the head, wherein the operable connection between the sleeve and the blade comprises an extension extending from the sleeve to the head, the extension engaging a wheel on the head wherein movement of the sleeve and extension along the first axis rotates the wheel and head about the second axis.

4. The device of claim 1, further comprising a housing, the drive shaft extending into the housing, at least a portion of the sleeve being mounted in the housing for movement in the housing, the sleeve being operably connected to the blade, a tube on the outside of a portion of the sleeve, the tube having a first position generally inside a portion of the housing and a second position distal to the first position, a driver connectable to the tube whereby movement of the driver moves the tube between its first and second positions.

5. The device of claim 1, further comprising movement means operably connected to the sleeve for urging the sleeve to move along the first axis relative to the drive shaft.

6. The device of claim 5, wherein the movement means comprises a slot through the drive shaft, the sleeve comprising a pin extending through slot to slide relative to the slot.

7. The device of claim 1, further comprising at least one slot through the drive shaft, a pin on the sleeve extending through the slot, wherein the pin moves along the slot as the sleeve moves relative to the drive shaft.

8. The device of claim 1, wherein the linkage comprises a sleeve coaxial with at least part of the drive shaft, the sleeve being movable along the first axis, and further comprising a head, the blade being mounted on the head, wherein the operable connection between the sleeve and the blade comprises at least one arm having a first end attached to the sleeve and a second end attached to the head, each arm being angled to the first axis, the sleeve being operably connected to the blade, whereby movement of the sleeve pivots the blade about the second axis, the device further comprising at least one proximal slot through the drive shaft and a distal slot through the drive shaft, a first pin on the sleeve extending through the proximal slot, wherein the first pin moves along the proximal slot as the sleeve moves relative to the drive shaft, a second pin on the sleeve extending through the distal slot, wherein the second pin moves along the distal slot as the sleeve moves relative to the drive shaft and wherein the first end of the arm mounts on the second pin.

9. The device of claim 8, wherein the second pin is positioned in the path of the sleeve as the sleeve moves along the first axis.

10. The device of claim 1, further comprising an alignment head positionable in the acetabular cup, the alignment head having an opening for receiving the distal end of the drive shaft, a stop in the alignment head for blocking the distal end of the drive shaft from reaching the acetabular cup when the alignment head is positioned in the acetabular cup.

11. The device of claim 1, wherein the blade has an inner surface facing the second axis, and an outer surface opposite the inner surface, at least one tooth extending from the outer surface of the blade, the tooth having a cutting surface angled away from the outer surface of the blade.

12. The device of claim 1, further comprising an alignment head positionable in the acetabular cup, the alignment head having an opening for receiving the distal end of the drive shaft, wherein the linkage is operably connected to the alignment head, the linkage pivoting the blade about the second axis such that the cutting edge of the blade extends between the acetabular cup and the hipbone as the drive shaft rotates the blade.

13. The device of claim 12, wherein the opening of the alignment head and the slot of the blade are aligned with each other.

14. A device for extracting a prosthetic acetabular cup attached to a hipbone comprising:
   a housing and a motor mounted to the housing;
   a drive shaft having a proximal end operably connected to the motor and a distal end spaced from the proximal end, the motor rotating the drive shaft about a first axis at the drive shaft's longitudinal axis;
   a head mounted near the distal end of the drive shaft, the head being connectable to a blade and being pivotably mounted to the drive shaft for rotation about a second axis generally perpendicular to the first axis;
   the blade being hemispherically shaped and having a distal end and a proximal end, the distal end having a cutting surface substantially about the blade, and the blade having a slot extending from and through the distal end toward the proximal end of the blade, and
   linkage means associated with the drive shaft for pivoting the head about the second axis.

15. The device of claim 14, wherein the linkage means comprises a sleeve extending about at least a portion of the drive shaft and being operably connected to the head, the sleeve being moveable along the first axis whereby movement of the sleeve along the first axis pivots the head about the second axis.

16. The device of claim 14, wherein the linkage means comprises a sleeve coaxial with at least part of the drive shaft, the sleeve being movable along the first axis, the sleeve being operably connected to the head, whereby movement of the sleeve pivots the head about the second axis.

17. The device of claim 16, wherein the linkage means further comprises at least one arm extending from the sleeve to the head, the at least one arm being angled relative to the first axis.

18. The device of claim 14, wherein the linkage means comprises a sleeve extending about a portion of the drive shaft and being operably connected to the head and wherein the head further comprises a slot, the drive shaft extending through the slot.

19. The device of claim 14, wherein the drive shaft extends into the housing and wherein the linkage means comprises a sleeve at least partially surrounding at least part of the drive shaft, the sleeve being mounted in the housing for movement along the first axis, the sleeve being operably connected to the head at a position on the head whereby movement of the sleeve pivots the head about the second axis.

20. The device of claim 14, wherein the linkage means comprises a sleeve coaxial with at least part of the drive shaft, the sleeve being movable along the first axis and being operably connected to the head, the linkage means further comprising at least one arm extending between the sleeve and the head and angled with respect to the first axis, whereby movement of the sleeve moves the arm to pivot the head about the second axis.

21. The device of claim 14, further comprising at least one distal slot through the drive shaft, a pin on the sleeve extending through the distal slot, wherein the pin moves along the distal slot as the sleeve moves relative to the drive shaft and wherein the first end of the arm mounts on the pin.

22. The device of claim 21, wherein the pin is positioned in the path of the sleeve as the sleeve moves along the first axis.

23. The device of claim 14, wherein the head has a distal end extending away from the distal end of the drive shaft, the cutting surface of the blade being aligned with the distal end of the head.

24. The device of claim 14, wherein, the drive shaft extends into the housing, the device further comprising a sleeve extending around at least a portion of the drive shaft, a portion of the sleeve being mounted in the housing for movement in the housing, the sleeve being operably connected to the blade, a tube on the outside of a portion of the sleeve, the tube having a first position generally inside a portion of the housing and a second position distal to the first position, a driver connectable to the tube whereby movement of the driver moves the tube between its first and second positions.

25. The device of claim 14, wherein the linkage means comprises a sleeve coaxial with and extending around at least part of the drive shaft, the sleeve being movable along the first axis, the sleeve being operably connected to the head, the linkage means further comprising at least one arm extending between the sleeve and the head and angled with respect to the first axis, whereby movement of the sleeve moves the arm to pivot the head about the second axis.

26. The device of claim 14, wherein the head has an opening for receiving the distal end of the drive shaft, the device further comprising an alignment head positionable in the acetabular cup, the alignment head having an opening for receiving the distal end of the drive shaft, a stop in the alignment head for blocking the distal end of the drive shaft from reaching the acetabular cup when the alignment head is positioned in the acetabular cup.

27. The device of claim 14, wherein the blade has an inner surface facing the second axis, and an outer surface opposite the inner surface, at least one tooth extending from the outer surface of the blade, the tooth having a cutting surface angled away from the outer surface of the blade.

28. The device of claim 26, wherein the opening of the head and the slot of the blade are aligned with each other.

29. A powered device for extracting a prosthetic acetabular cup attached to a hipbone comprising:
   a housing and a motor mounted to the housing;
   a drive shaft having a proximal end operably connected to the motor and a distal end spaced from the proximal end, the motor rotating the drive shaft about a first axis corresponding to the longitudinal axis of the drive shaft, the drive shaft being fixed longitudinally in the housing;

a head having a proximal end mounted near the distal end of the drive shaft and a distal end opposite the proximal end, a blade having a hemispheric shape, and having a distal end and a proximal end, the distal end having a cutting surface extending substantially about the blade, and the blade having a slot extending from and through the distal end toward the proximal end of the blade, the blade being connected to the head, the head being pivotably mounted to the drive shaft for rotation about a second axis generally perpendicular to the first axis;

a sleeve coaxial with and rotating with the drive shaft; and linkage means associated with the sleeve and head for pivoting the head about a second axis perpendicular to the first axis.

30. The device of claim 29, wherein the linkage means comprises at least one slot through the drive shaft, a pin on the sleeve extending through the slot, at least one arm having a first end attached to the pin and a second end attached to the head; the sleeve engaging the pin as the sleeve moves along the first axis, wherein the second end of the arm is spaced from the first axis.

31. The device of claim 23, wherein the distal end of the head is hemispherical, and the blade conforms to the distal end of the head.

32. The device of claim 29, wherein the head has a distal end extending away from the distal end of the drive shaft, the blade having a cutting surface aligned with the distal end of the head.

33. The device of claim 32, wherein the distal end of the head is hemispherical, and the blade conforms to the distal end of the head.

34. The device of claim 29, wherein the drive shaft extends into the housing, a portion of the sleeve being mounted in the housing for movement in the housing, the sleeve being operably connected to the blade, a tube on the outside of a portion of the sleeve, the tube having a first position generally inside a portion of the housing and a second position distal to the first position, a driver connectable to the tube whereby movement of the driver moves the tube between its first and second positions.

35. The device of claim 29, wherein the sleeve is movable along the first axis and is operably connected to the head, the linkage means further comprising at least one arm extending between the sleeve and the head and angled with respect to the first axis, whereby movement of the sleeve moves the arm to pivot the head about the second axis.

36. The device of claim 29, further comprising an alignment head positionable in the acetabular cup, the alignment head having an opening for receiving the distal end of the drive shaft, a stop in the alignment head for blocking the distal end of the drive shaft from reaching the acetabular cup when the alignment head is positioned in the acetabular cup.

37. The device of claim 29, wherein the blade has an inner surface facing the second axis, and an outer surface opposite the inner surface, at least one tooth extending from the outer surface of the blade, the tooth having a cutting surface angled away from the outer surface of the blade.

38. A device for extracting a prosthetic acetabular cup attached to a hipbone, the device comprising:

a head having a proximal end and a distal end;

a blade having hemispherical shape, a distal end of the hemispherical blade having a cutting edge and a slot extending from the distal end toward its proximal end;

a drive shaft having distal and proximal ends and a first axis longitudinal with the drive shaft, the proximal end being operably connected to a motor for rotating the drive shaft about the first axis and the drive shaft extending through the slot, the head being mounted near the distal end of the drive shaft for pivoting about a second axis generally perpendicular to the first axis; and a linkage operably connected to the head, the linkage pivoting the blade about the second axis such that the cutting edge of the blade extends between the acetabular cup and the hipbone as the drive shaft rotates the blade.

\* \* \* \* \*